US010394928B2

(12) United States Patent
Yen et al.

(10) Patent No.: US 10,394,928 B2
(45) Date of Patent: Aug. 27, 2019

(54) CORNEAL DYNAMIC MODEL ALGORITHM AND SYSTEM USING THE SAME

(71) Applicant: National Taiwan University, Taipei (TW)

(72) Inventors: Jia-Yush Yen, Taipei (TW); Po-Jen Shih, Kaohsiung (TW); Chun-Ju Huang, Taipei (TW); Hui-Jun Cao, Kaohsiung (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 635 days.

(21) Appl. No.: 15/073,381

(22) Filed: Mar. 17, 2016

(65) Prior Publication Data

US 2016/0275264 A1 Sep. 22, 2016

Related U.S. Application Data

(60) Provisional application No. 62/134,438, filed on Mar. 17, 2015.

(51) Int. Cl.
*G06F 17/10* (2006.01)
*G06F 17/13* (2006.01)
*G16H 50/50* (2018.01)

(52) U.S. Cl.
CPC ............ *G06F 17/13* (2013.01); *G16H 50/50* (2018.01)

(58) Field of Classification Search
CPC .................................. G06F 17/13; G16H 50/50
USPC ............................................................ 703/2
See application file for complete search history.

(56) References Cited

U.S. PATENT DOCUMENTS

| 2011/0118585 A1* | 5/2011 | Ishii .................. A61B 3/16 600/401 |
| 2012/0220850 A1* | 8/2012 | Umekawa .......... A61B 3/0041 600/401 |
| 2013/0184554 A1 | 7/2013 | Elsheikh et al. |

FOREIGN PATENT DOCUMENTS

CN           103415244 A           11/2013

OTHER PUBLICATIONS

Hamilton et al. (Young's Modulus in Normal Corneas and the effect on Applanation Tomometry, 6 pages). (Year: 2008).*
Elsheikh et al. (Determination of the Modulus of Elasticity of the Human Cornea, 12 pages. (Year: 2007).*

* cited by examiner

*Primary Examiner* — Andre Pierre Louis
(74) *Attorney, Agent, or Firm* — Muncy, Geissler, Olds & Lowe, P.C.

(57) ABSTRACT

A corneal dynamic model algorithm and system using the same is provided, comprising an ophthalmotonometer and a calculating unit. The calculating unit comprises the algorithm for calculating the corneal dynamic model. The algorithm comprises: reading an actual corneal deformation from the ophthalmotonometer; substituting a young's modulus initial value and a damping coefficient initial value into a mathematical equation for getting a calculated corneal deformation; determining whether error amount between the calculated deformation and the actual deformation is a minimum or not; and getting a young's modulus and a damping coefficient.

6 Claims, 7 Drawing Sheets

CORNEAL DYNAMIC MODEL ALGORITHM AND SYSTEM USING THE SAME

CROSS REFERENCE TO RELATED APPLICATIONS

This application is a non-provisional application which claims priority of U.S. Provisional Application No. 62/134,438 filed on Mar. 17, 2015 under 35 U.S.C. § 119(e), the entire contents of all of which are hereby incorporated by reference.

BACKGROUND OF THE INVENTION

1. Field of the Invention

The present invention relates to a corneal dynamic model algorithm and system using the same. Specially, it is an instantaneous and non-invasive corneal dynamic model algorithm and system using the same.

2. Description of the Prior Art

As technology advances, it also drives the speedy development of computers, televisions, mobile phones and other digital merchandises. The long hours of using eyes on surfing internet, watching TV, operating the mobile phone cause eyes dry, photophobia, tearing, fatigue, and even with conditions that are accompanied with symptoms of headache, dizziness, nausea, shoulder and neck pain, blurred vision. As a result, eye fatigue has become a common civilization disease of people in the modern society.

Overuse of eyes can result in abnormal function of focus adjustment, loss of efficacy in adjusting the focus length precisely, blurred vision, aggravating myopia, xerophthalmia, or eye diseases such as induced glaucoma and retinal lesion.

Therefore, in addition to a timely rest for the eyes, regular examination of the eyes is particularly important. The advanced intra-ocular pressure (IOP) detector is the Corvis® ST of Oculus in Germany. The Corvis® ST is a non-invasive ophthalmotonometer. It uses the high-speed photographic technology to snap 140 corneal sectional images within 31 ms, and calculate and analyze data, including the degree of applanation and rebound when a specific amount of air pressure is blown onto the eye and the speed, in order to evaluate biomechanical characteristics of the cornea.

So far the Corvis® ST in medical science only applies to detect IOP, cornealectasia, and collagen crosslinking. However, it cannot detect instantaneously the Young's modulus of cornea.

SUMMARY OF THE INVENTION

In view of the above problems, in one aspect, the present invention provides a dynamic model for analyzing the mechanical properties instantaneously when receiving the images from the ophthalmotonometer.

In one embodiment, the present invention provides a corneal dynamic model algorithm, comprising: (S1) reading an actual corneal deformation from an ophthalmotonometer; (S2) substituting a young's modulus initial value and a damping coefficient initial value into a mathematical equation for getting a calculated corneal deformation; (S3) determining whether error amount between the calculated deformation and the actual deformation is a minimum or not; and (S4) getting a young's modulus and a damping coefficient.

Wherein if the determining in the step (S3) is not, then back to the step (S2) and iterate in optimization until the error amount is a minimum.

In this embodiment, the mathematical equation is $$w(\theta, \phi; t) = \sum_{l=1}^{\infty} w_{l0}(\theta, \phi; t).$$

In this embodiment, the minimum is $10^{-3}$.

In another aspect, the present invention provides a corneal dynamic model system, comprising an ophthalmotonometer and a calculating unit. The calculating unit comprises the algorithm for calculating the corneal dynamic model. The algorithm comprises: (S1) reading an actual corneal deformation from the ophthalmotonometer; (S2) substituting a young's modulus initial value and a damping coefficient initial value into a mathematical equation for getting a calculated corneal deformation; (S3) determining whether error amount between the calculated deformation and the actual deformation is a minimum or not; and (S4) getting a young's modulus and a damping coefficient.

Wherein if the determining in the step (S3) is not, then back to the step (S2) and iterate in optimization until the error amount is a minimum.

In this embodiment, the mathematical equation is $$w(\theta, \phi; t) = \sum_{l=1}^{\infty} w_{l0}(\theta, \phi; t).$$

In this embodiment, the minimum is $10^{-3}$.

The following description and the drawings set forth certain illustrative advantages and spirits of the specification.

DETAILED DESCRIPTION OF THE PREFERRED EMBODIMENT

Figure 1A:
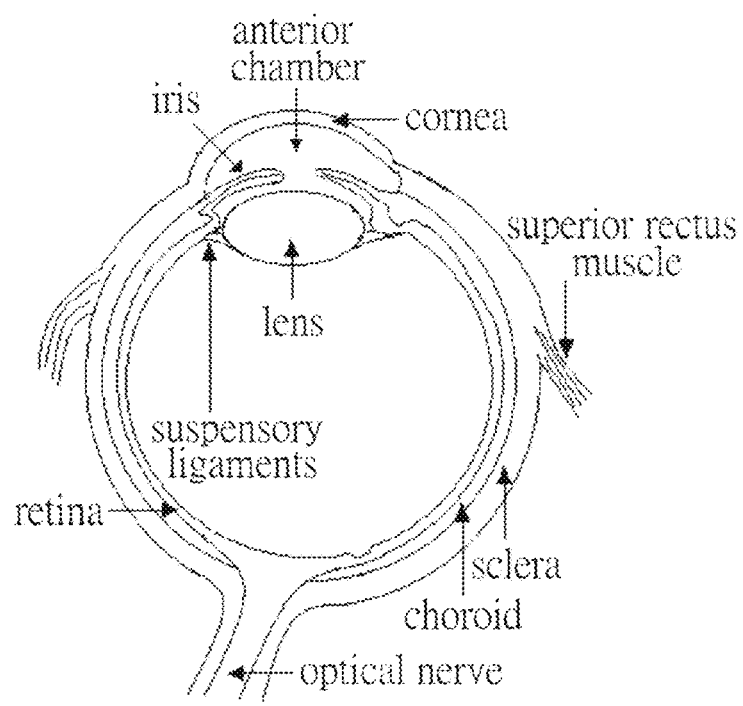
FIG. 1A is a schematic diagram of an eyeball.

The following will disclose a plurality of embodiment with texts and drawings. For a clear illustration, many details in practice will be described in the following description. However, it should be understand that the details of the practical application of these are not to limit the present invention. In addition, for the sake of simplifying the drawings, some of the conventional structures and components in the drawings will be depicted in a simplified schematic manner.

In order to implement this invention, we simply the eyeball structure. There are eight assumptions setup through this invention. As shown in FIG. 1A, the eye is made up of the three layers and the three transparent structures. The outermost layer is composed of the cornea and sclera, the middle layer is consists of the choroid, ciliary body (not indicated), and iris, and the innermost is the retina. The eight basic assumptions are made: (i) the eyeball is a perfectly spherical diaphragm, and fluid is completely filled inside the eyeball; (ii) the thickness and material of the diaphragm are uniform everywhere. Here we take the corneal properties as the material of diaphragm; (iii) the amplitude of oscillation is small compared with the characteristic length of the eyeball; (iv) the fluid inside the eyeball is incompressible water; (v) the iris is neglected because of its relatively small volume; (vi) the space of lens is regarded as fluid because of its density is closed to fluid; (vii) the air impulsion applies on the cornea with a Gaussian distribution; (viii) boundary conditions at the surface outside the eyeball is free movement.

Figure 1B:
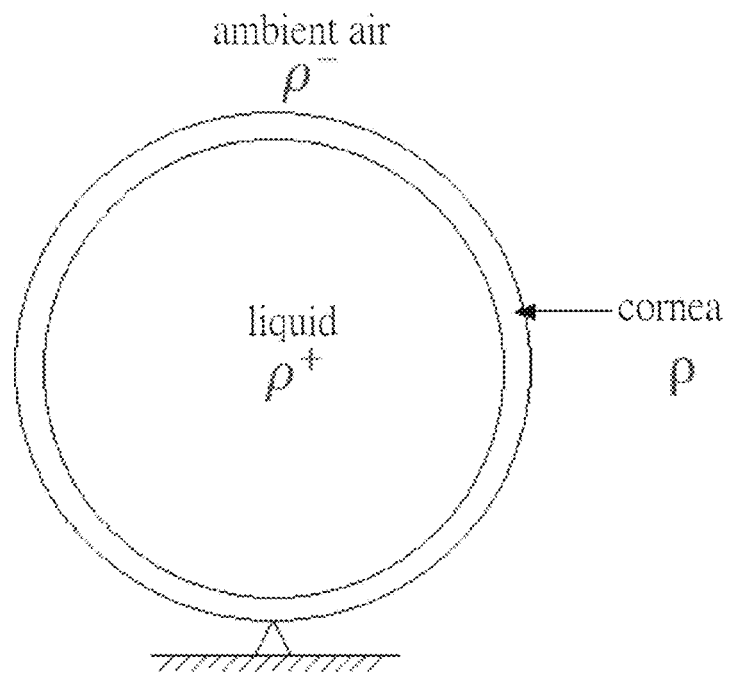
FIG. 1B is a schematic diagram of an eyeball dynamic model in one embodiment.
Figure 2A:
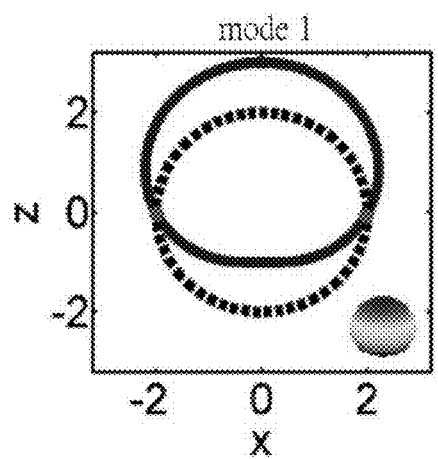
FIG. 2A-FIG. 2F are schematic diagrams of the first six model shapes of the eyeball model in one embodiment.
Figure 2B:
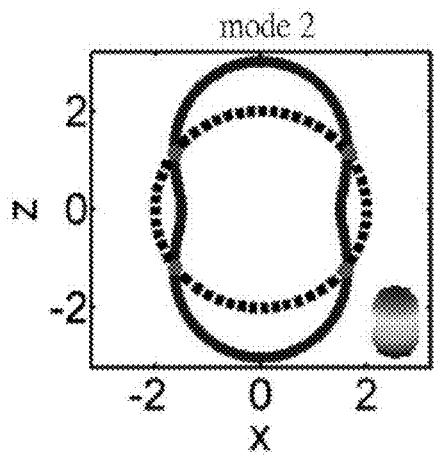
Figure 2C:
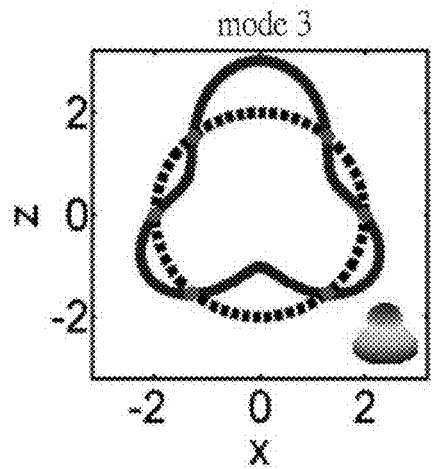
Figure 2D:
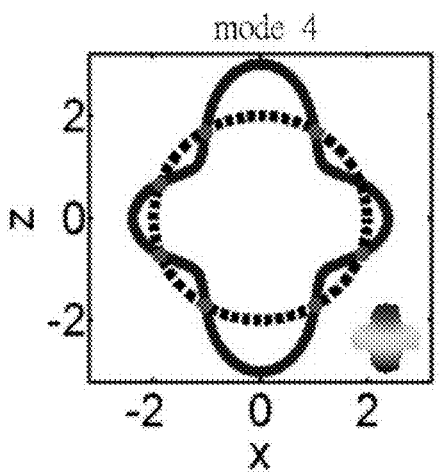
Figure 2E:
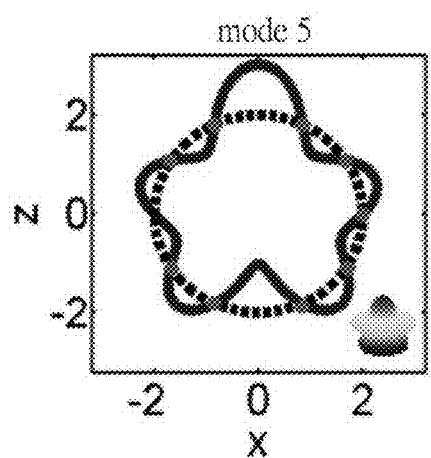
Figure 2F:
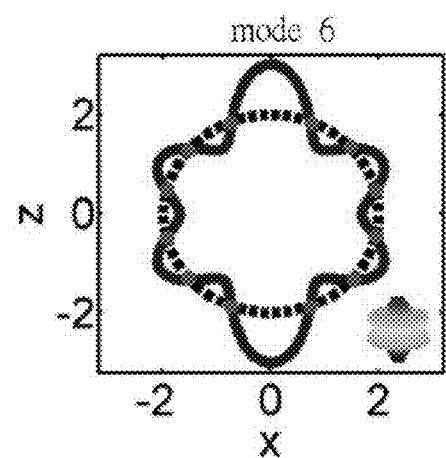
Figure 3:
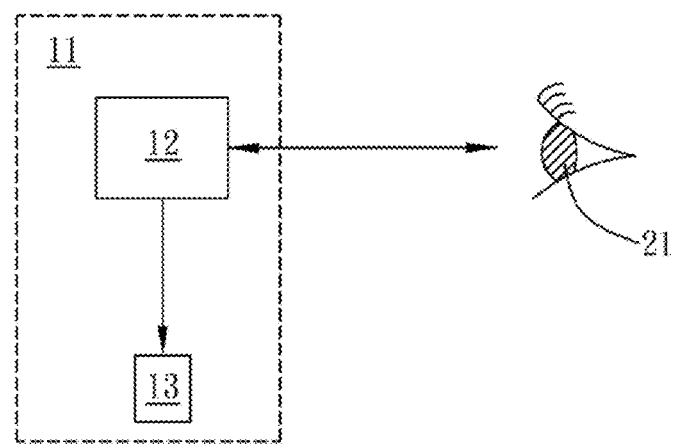
FIG. 3 is a schematic diagram of a corneal dynamic model system in one embodiment.

As shown in FIG. 1B, this model simplifies the eyeball into the three parts: the air outside the eyeball (the oblique and rectus muscles are not concerned), the diaphragm of the eyeball (including cornea, sclera and retina), and the fluid inside the eyeball (including vitreous humor, lens, and aqueous humor.) Here, we have three steps to derive the modal frequencies of the eyeball.

Firstly, the spherical surface harmonics and radiation functions help develop the pressure functions outside and inside the eyeball. The Euler's equation for the ambient air and the fluid inside the eyeball is $$\begin{cases} \frac{\partial v}{\partial t} + v \cdot \nabla v = -\frac{1}{\rho} \nabla p \\ \nabla \cdot v = 0 \end{cases} \quad \text{(eq. 1)}$$

Wherein $v_i$ is the covariant component of velocity fields, $\rho$ is the density, p is the pressure, and we neglect the fluid viscosity. In the spherical coordinates system (r, θ, φ, the linearized hydrodynamic equation with velocity in r direction is $$\frac{\partial v_r}{\partial t} = -\frac{1}{\rho} \frac{\partial p}{\partial r}. \quad \text{(eq. 2)}$$

The solution of $p^+$ inside the eyeball is given by $$p^+ = \sum_{l=0}^{\infty} \sum_{m=-l}^{-l} i\rho^+ R^2 \omega^2 A_{lm}^+ Y_{lm}(\theta, \phi) \left(\frac{r}{R}\right)^l e^{i\omega t}. \quad \text{(eq. 3)}$$

With undetermined constants $A_{lm}^+$ and where the angular frequency ω, R is the radius of eyeball, and $Y_{lm}$ are the spherical surface harmonics.

Note that the superscript '+' denotes the domain inside the eyeball. The Fourier transform of functions with respective to time t is given by $\hat{x}(\omega) = \int_{-\infty}^{\infty} x(t) e^{i\omega t} dt$. So that the solution of $p^-$ outside the eyeball is $$p^- = \sum_{l=0}^{\infty} \sum_{m=-l}^{-l} i\rho^- R^2 \omega^2 A_{lm}^- Y_{lm}(\theta, \phi) \left(\frac{r}{R}\right)^{-l-1} e^{i\omega t}. \quad \text{(eq. 4)}$$

Here the air and fluid are assumed to be incompressible, so the zeroth harmonic $Y_{00}(\theta, \phi)$ is excluded. The velocity component on the surface, i.e. r=R, becomes $$\begin{aligned} V_R(r, \theta, \phi; t) &= \sum_{l=0}^{\infty} \sum_{m=-l}^{-l} -\rho^- R^2 \omega A_{lm}^+ Y_{lm}(\theta, \phi) e^{i\omega t} \\ &= \sum_{l=0}^{\infty} \sum_{m=-l}^{-l} -\rho^- R^2 \omega A_{lm}^- Y_{lm}(\theta, \phi) e^{i\omega t}. \end{aligned} \quad \text{(eq. 5)}$$

Note that the series expansion of both air and fluid are substantially setup on the orthogonal and complete sets.

Secondly, the modified Helmholtz function helps derive the displacement function on the stretched diaphragm. The stretched diaphragm with tension and stiffness has a potential energy of bending which is determined by the tension of the diaphragm, fluid pressure, and the elastic constants of the material. The intraocular pressure let the diaphragm be stretched tightly, and the quantity of tension is 10-20% of the stiffness of the material of the diaphragm. Because the added tension increases the effective modulus, the added term T to the Young's modulus occurs. Hence the modified Helmholtz equation satisfied for points at the surface is $$\frac{(E+T) \cdot t^3}{12(1-v^2)} \nabla^4 w - T \cdot t \nabla^2 w - [p] + \rho \cdot t \frac{\partial^2 w}{\partial t^2} = 0. \quad \text{(eq. 6)}$$

Wherein E is the Young's modulus, T is the tension on the diaphragm, t is the thickness of the diaphragm, v is the Poisson's ratio, ρ is the density of the diaphragm, and [p] is the pressure difference between the two sides of the diaphragm, i.e. $[p]=p^+-p^-$. For the case of a spherical diaphragm, the Laplacian of w on sphere with (r, θ, φ) are $$\nabla^2 = \frac{1}{r^2} \left[ \frac{1}{\sin\theta} \frac{\partial}{\partial \theta} \left( \sin\theta \frac{\partial}{\partial \theta} \right) + \frac{1}{\sin^2\theta} \frac{\partial^2}{\partial \phi^2} \right]. \quad \text{(eq. 7)}$$

We assume the simple harmonic motion is the solution of this equation, $$w(\theta, \phi; t) = \sum_{l=0}^{\infty} \sum_{m=-l}^{l} w_{lm}(\theta, \phi; t) \quad \text{(eq. 8)}$$
$$= \sum_{l=0}^{\infty} \sum_{m=-l}^{l} -iB_{lm}Y_{lm}(\theta, \phi) \cdot e^{i\omega t}.$$

Wherein $B_{lm}$ are the undetermined constants. Note that the series expansion of the diaphragm is substantially setup on the orthogonal and complete bases.

Thirdly, the continuities on the interfaces help to develop the characteristic function. There are two radial conditions of velocities ensure the continuous on the interfaces between the air-diaphragm and the diaphragm-liquid:

$$v_R^+ = \dot{w} \quad \text{(eq. 9)}$$

$$v_R^- = \dot{w} \quad \text{(eq. 10)}.$$

Substituting Eqs. (4), (5), and (8) into Eqs. (9) and (10) leads the relationships with three unknowns $A_{lm}^+$, $A_{lm}^-$, and $B_{lm}$:

$$lRA_{lm}^+ + B_{lm} = 0 \quad \text{(eq. 11)}$$

$$(l+1)RA_{lm}^- - B_{lm} = 0 \quad \text{(eq. 12)}.$$

Moreover, using Eqs. (3) and (4), replacing the coefficients of $A_{lm}^+$ and $A_{lm}^-$ by $B_{lm}$, and modifying the pressure difference term [p] at the diaphragm lead $$[p]_{lm} = -iR\omega^2 B_{lm} Y_{lm}(\theta, \phi) e^{i\omega t} \left( \frac{\rho^+}{l} + \frac{\rho^-}{l+1} \right). \quad \text{(eq. 13)}$$

Furthermore, the second differentiation of the displacement from Eq. (8) is $$\frac{\partial^2 w_{lm}}{\partial t^2} = i\omega^2 B_{lm} Y_{lm}(\theta, \phi) e^{i\omega t}. \quad \text{(eq. 14)}$$

So that the pressure difference can be rewritten to $$[p]_{lm} = -R\left( \frac{\rho^+}{l} + \frac{\rho^-}{l+1} \right) \frac{\partial^2 w_{lm}}{\partial t^2}. \quad \text{(eq. 15)}$$

Substituting Eq. (15) into Eq. (6) leads the new modal motion equation $$\left[ \frac{(E+T) \cdot t^3}{12(1-v^2)} \frac{l^2(l+1)^2}{R^4} + \frac{l(l+1)T \cdot t}{R^2} \right] w_{lm} + \left[ \rho \cdot t + R\left( \frac{\rho^+}{l} + \frac{\rho^-}{l+1} \right) \right] \frac{\partial^2 w_{lm}}{\partial t^2} = 0. \quad \text{(eq. 16)}$$

Wherein the relation of $R^2 \nabla^2 w_{lm} = -l(l+1)w_{lm}$ is used. Then it is obviously the natural frequency term becomes $$\omega_l^2 = \frac{\frac{(E+T) \cdot t^3}{12(1-v^2)} \frac{l^3(l+1)^3}{R^4} + \frac{T \cdot t \cdot l^2(l+1)^2}{R^2}}{[(l+1)\rho^+ + l \cdot p^-]R + l(l+1)\rho \cdot t}. \quad \text{(eq. 17)}$$

Thus the modal frequency is $f_l = \omega_l / 2\pi$.

Moreover, Eq. (17) can be rewritten into $$M_l \frac{\partial^2 w_{lm}}{\partial t^2} + K_l w_{lm} = 0. \quad \text{(eq. 18)}$$

Wherein the modal masses are $$M_l = \rho \cdot t + R\left( \frac{\rho^+}{l} + \frac{\rho^-}{l+1} \right),$$

and modal spring constants are $$K_l = \frac{(E+T) \cdot t^3}{12(1-v^2)} \frac{l^2(l+1)^2}{R^4} + \frac{l(l+1)T \cdot t}{R^2}.$$

In the previous discussion, the modal equation of motion is given. The forced vibration also could be extended in modal analysis. While the external force term $F_{lm}$ the damping term $C_l \dot{w}_{lm}$ are added in Eq. (18), the equation of motion of the system becomes $$M_l \frac{\partial^2 w_{lm}}{\partial t^2} + C_l \frac{\partial w_{lm}}{\partial t} + K_l w_{lm} = F_{lm}. \quad \text{(eq. 19)}$$

Note that the damping comes from the viscosity of water and the structural diaphragm. But the certain values of the dampers are difficult to be obtained. So we just put damper coefficients as the undetermined coefficients, and then we will use numerical technique to estimate them.

Here the series expansion of the external force is defined by $$F(\theta, \phi; t) = \sum_{l=0}^{\infty} \sum_{m=-l}^{l} F_{lm} Y_{lm}(\theta, \phi) e^{i\omega t}. \quad \text{(eq. 20)}$$

Wherein $$F_{lm} = \frac{\int_0^{2\pi} \int_0^{\pi} F(\theta, \phi; t) Y_{lm}(\theta, \phi) \sin\theta \, d\theta \, d\phi}{\int_0^{2\pi} \int_0^{\pi} Y_{lm}^2(\theta, \phi) \sin\theta \, d\theta \, d\phi}. \quad \text{(eq. 21)}$$

Then solution of Eq. (19) is $$w_{lm}(\theta, \phi; t) = \frac{1}{M_l} e^{-\xi_l \omega_{Dl} t} \int_0^t \frac{\sin \omega_{Dl}(t-\tau)}{\omega_{Dl}} F_{lm} d\tau \cdot Y_{lm}(\theta, \phi),\quad \text{(eq. 22)}$$

in which the damping ratio is defined by $\xi_l = C_l/M_l$ and $\omega_{Dl} = \omega\sqrt{1-\xi^2}$.

Moreover, the external force is a symmetric force about the $\theta=0$ axis, namely $F(\theta, \phi', t) = g(\theta)h(t)$. That means $m=0$, and the surface harmonics could be simplified by $Y_{l0} = P_l(\cos \theta)$. Then $$F_{l0} = (l+\tfrac{1}{2})\int_0^\pi g(\theta)P_l(\theta)\sin\theta d\theta \cdot h(t) \quad \text{(eq. 23)}$$

The integration, $\int_0^\pi [P_l(\cos\theta)]^2 \sin d\theta = 2/(2l+1)$, helps to solve the modal displacements $$w_{l0}(\theta, \phi; t) = \frac{(2l+1)}{2M_l \omega_{Dl}} P_l(\cos\theta) \cdot \int_0^\pi g(\alpha)P_l(\alpha)\sin\alpha\, d\alpha \cdot \int_0^t e^{-\xi\omega_{Dl}t}\sin\omega_{Dl}(t-\tau)h(t)d\tau, \quad \text{(eq. 24)}$$

and the total displacements at the diaphragm become $$w(\theta, \phi; t) = \sum_{l=1}^{\infty} w_{l0}(\theta, \phi; t). \quad \text{(eq. 25)}$$

It is noted that on the solution of the displacement at the diaphragm, there are two terms which should be solved before the numerical calculation: the modal shape functions of the diaphragm, the modal external force in spatial distribution and in time series. For the modal shape functions of the diaphragm, the surface harmonics $Y_{lm}(\theta,\phi)$ are the main terms of Eq. (8). Since the external force is axial symmetry and $m=0$, the modal shapes $[Y_{l0}=P_l(\cos\theta)]$ could be obtained from the definition of the Legendre polynomial function.

One embodiment in this application, please refer to FIG. 2A~FIG. 2F and FIG. 3. A corneal dynamic model system 11 preferably comprises an ophthalmotonometer 12 and a calculating unit 13. In this embodiment, the ophthalmotonometer 12 is Corvis® ST produced by Oculus, but not limited thereto. This ophthalmotonometer uses the high-speed photographic technology to snap 140 corneal sectional images within 31 ms, and calculate and analyze data, including the degree of applanation and rebound when a specific amount of air pressure is blown onto the eye and the speed, in order to evaluate biomechanical characteristics of the cornea. However, other ophthalmotonometers can be used in other embodiments. The calculating unit 13 can be a processor or other members with computing capability.

By directing an external force (e.g. air-puff) to the eye 21 with the ophthalmotonometer 12, the ophthalmotonometer 12 could obtain an actual corneal deformation Dt. Wherein when the eyeball is directed by the ophthalmotonometer 12, the first six model shapes of the eyeball model are shown in FIG. 2A~FIG. 2F. The red dots mark the nodal points and are regarded as the hinged conditions at the surface of the diaphragm.

Figure 4A:
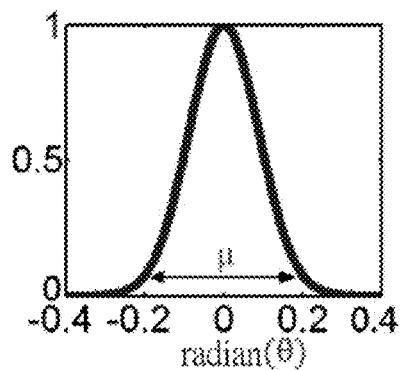
FIG. 4A is a schematic diagram of air pressure Gaussian distribution.
Figure 4B:
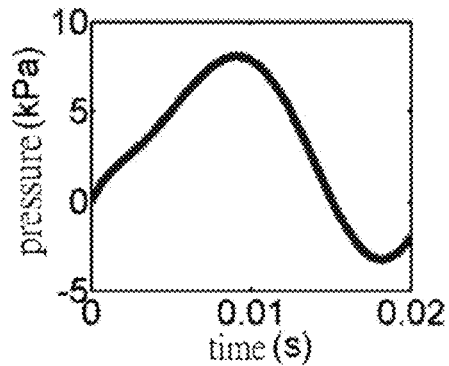
FIG. 4B is a schematic diagram of time series of the air pressure.

In addition, as shown in FIG. 4A, we assume the pressure distribution deduced from the ophthalmotonometer 12 is a three-dimensional Gaussian distribution. The width of the Gaussian distribution is by a parameter $\mu$. Besides, the time series of the air pressure measured by the experiment is shown in FIG. 4B.

Table I gives the material properties of the eyeball.

TABLE I

| Properties | Symbols | Values |
| --- | --- | --- |
| Radius | R | 12 mm |
| Thickness | t | 540 μm |
| Poisson's ratio | ν | 0.49 |
| Density of air | $\rho^-$ | 1.204 kg/m³ |
| Density of fluid inside eyeball | $\rho^+$ | 1000 kg/m³ |
| Density of sclera | ρ | 1444 kg/m³ |

Moreover, according to Eq. 18, the top 10 modal frequencies are listed on Table II.

TABLE II

| Mode No. | Frequency [Hz] |
| --- | --- |
| 1 | 14.363 |
| 2 | 33.0 |
| 3 | 55.657 |
| 4 | 82.109 |
| 5 | 112.336 |
| 6 | 146.437 |
| 7 | 184.576 |
| 8 | 226.951 |
| 9 | 273.771 |
| 10 | 325.246 |

Wherein the Young's modulus is assumed 0.48034 MPa and the IOP is 14.5 mmHg.

Figure 5A:
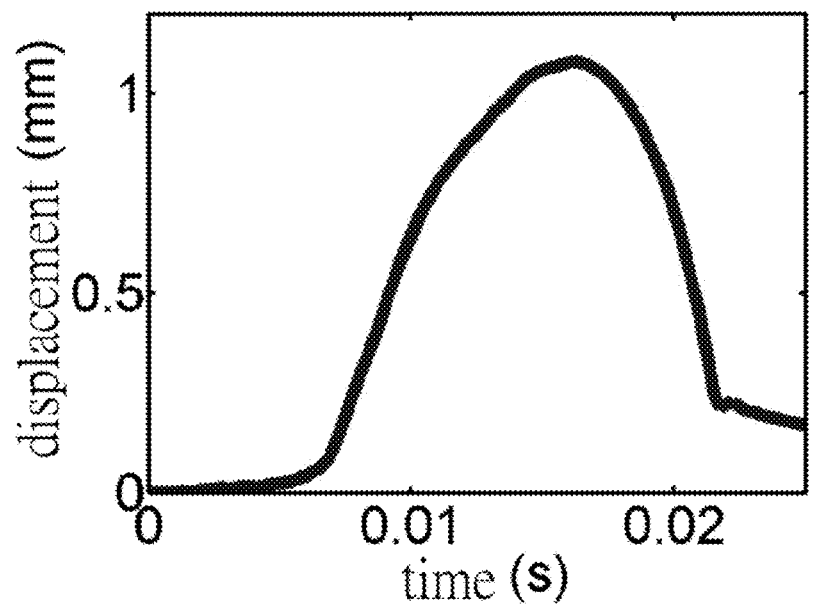
FIG. 5A is a schematic diagram of time series displacement at the top of cornea.
Figure 5B:
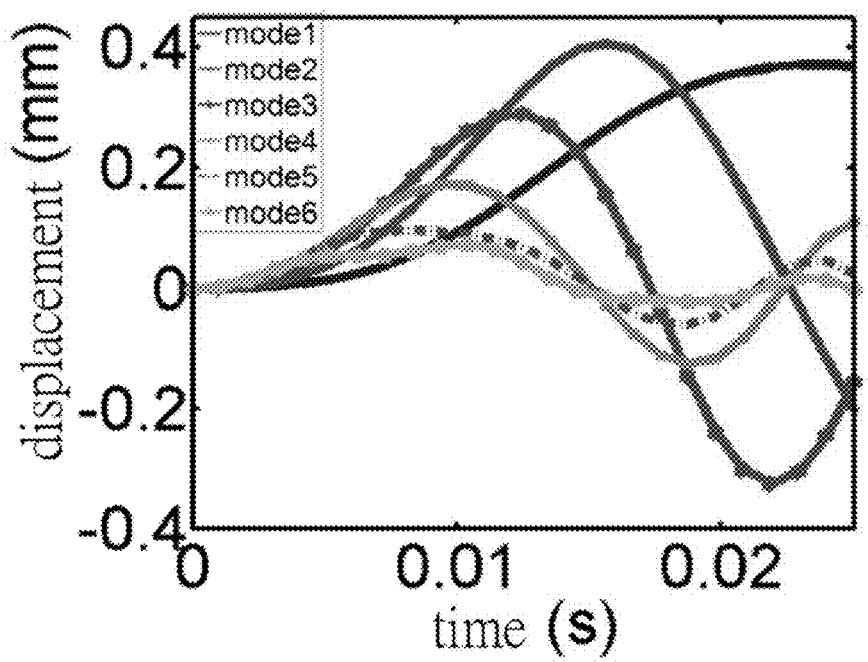
FIG. 5B is a schematic diagram of the first six modal time series displacement at the top of cornea.

In this case, Eq. 25 helps to obtain the displacements at the point as shown in FIG. 5A. The time series of the first six modes, denoting the eigen functions of Eq. 24 by the following equation 26, as shown in FIG. 5B. The eq. 26 is $$w_l(0,0;T) = P_l(1)\cdot\int_0^\pi g(\alpha)P_l(\alpha)\sin\alpha\, d\alpha \cdot \int_0^t e^{-\xi\omega_{Dl}t}\sin\omega_l(t-\tau)h(t)d\tau \quad \text{(eq. 26).}$$

It is noted that, before substituting the above parameters into the mathematical equation (i.e. Eq. 25), we need to assume initial values respectively for the Young's modulus and the damping coefficients. Wherein the assumed initial value can be a value based on the past experience or a value provided by the research work.

In above discussion, it is obviously that both of the Young's modulus and the damping coefficients affect the distribution shape of the corneal deformation. Here we compared the simulation displacements w(0,0;t) by applying Eq. (25) with these measured from the corneal displacement. Then we applied the optimization program (e.g. Matlab) to estimate the modal spring constants, $K_l$, and the modal damping coefficients, $C_l$.

Finding the error amount during the optimization program. That is, determine whether error amount between the calculated deformation and the actual deformation is a minimum or not. When the error amount is minimum, the Young's modulus and the damping coefficients can be obtained. It is noted that, when the error amount is determined not to be the minimal value, re-assume initial values respectively for the Young's modulus and the damping coefficients to calculate iteratively until the error value becomes the minimum value. In this embodiment, the minimum preferably is $10^{-3}$, but not limited thereto.

Figure 6:
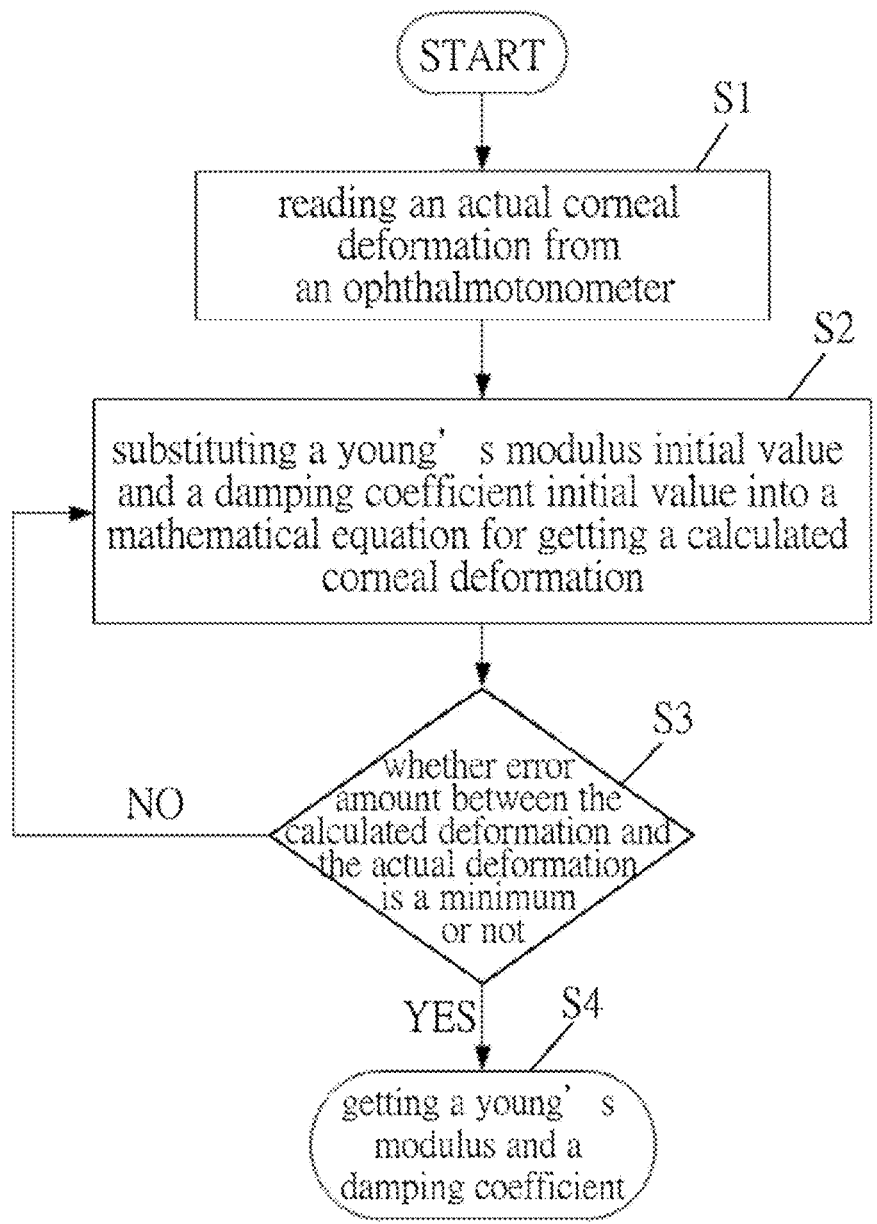
FIG. 6 is a flowchart of a corneal dynamic model algorithm in one embodiment.

As set forth above, the whole algorithm is shown in FIG. 6. The algorithm preferably is applied to the corneal dynamic model system above mentioned. The algorithm comprising: (S1) reading an actual corneal deformation from an ophthalmotonometer; (S2) substituting a young's modulus initial value and a damping coefficient initial value into a mathematical equation for getting a calculated corneal deformation; (S3) determining whether error amount between the calculated deformation and the actual deformation is a minimum or not; and (S4) getting a young's modulus and a damping coefficient. It is noted that, if step (S3) is determined not to be the minimal value, then return to step (S2) to calculate iteratively until the error value becomes the minimum value.

Note that this algorithm can be written/stored in the calculating unit 13 of the corneal dynamic model system by software or firmware. The calculating unit 13 could connect externally with the ophthalmotonometer. However, it could also be set in the ophthalmotonometer.

In practical application, there were 25 patients joined this study, and their information is listed on Table III.

TABLE III

| Patient No | Age | Thickness [μm] | IOP [mmHg] | Estimated Young's modulus [MPa] | Damping coefficients |
|---|---|---|---|---|---|
| 1 | 74 | 742 | 11 | 0.1178 | 0.0498 |
| 2 | 23 | 545 | 16 | 0.1102 | 0.0471 |
| 3 | 40 | 565 | 13 | 0.0103 | 0.0372 |
| 4 | 26 | 459 | 12.5 | 0.6644 | 0.0437 |
| 5 | 28 | 558 | 14 | 0.1122 | 0.0446 |
| 6 | 36 | 585 | 14.5 | 0.1204 | 0.0594 |
| 7 | 50 | 578 | 13 | 0.1411 | 0.1 |
| 8 | 26 | 596 | 14.5 | 0.1074 | 0.0355 |
| 9 | 39 | 564 | 15 | 0.1114 | 0.0144 |
| 10 | 38 | 525 | 12 | 0.205 | 0.0346 |
| 11 | 33 | 501 | 13 | 0.1301 | 0.083 |
| 12 | 27 | 565 | 14 | 0.7325 | 0.133 |
| 13 | 26 | 529 | 15 | 0.2909 | 0.0336 |
| 14 | 49 | 518 | 16 | 0.1347 | 0.035 |
| 15 | 24 | 577 | 16.5 | 0.5288 | 0.033 |
| 16 | 35 | 547 | 15 | 0.2651 | 0.0343 |
| 17 | 27 | 651 | 17 | 0.1022 | 0.0356 |
| 18 | 51 | 584 | 15.5 | 0.026 | 0.033 |
| 19 | 25 | 506 | 13 | 0.5701 | 0.0329 |
| 20 | 42 | 454 | 11.5 | 0.6149 | 0.0329 |
| 21 | 22 | 544 | 14 | 1.2427 | 0.0323 |
| 22 | 36 | 497 | 16 | 1.0056 | 0.0549 |
| 23 | 22 | 571 | 12.5 | 0.2686 | 0.0305 |
| 24 | 39 | 476 | 12 | 0.0739 | 0.0342 |
| 25 | 26 | 555 | 13 | 0.2708 | 0.0348 |
| Average | 34.56 | 551.68 | 13.98 | 0.3183 | 0.0456 |

Figure 7:
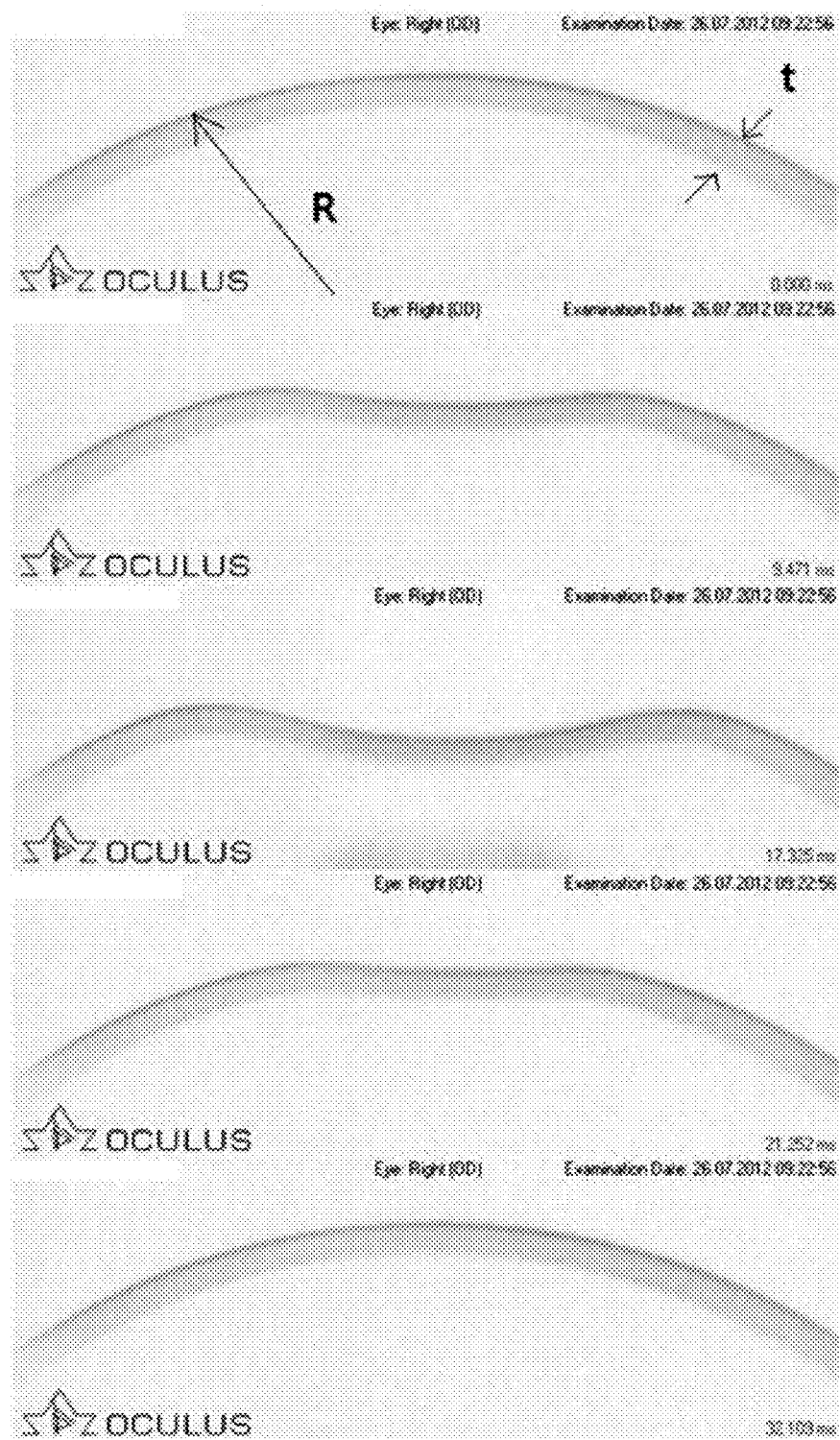
FIG. 7 is corneal images taken from one patient by the ophthalmotonometer.

In this study, parts of the material properties were assumed and shown on Table I, except the thicknesses. The values IOPs and the thicknesses could be measured from the ophthalmotonometer 12. As shown in FIG. 7, the displacements of the cornea of one patient at time 0.000, 9.471, 17.325, and 21.252 msec. Besides, the vibration information of cornea can be obtained by technique of image modeling and analysis from images before and during the air-puff.

Figure 8A:
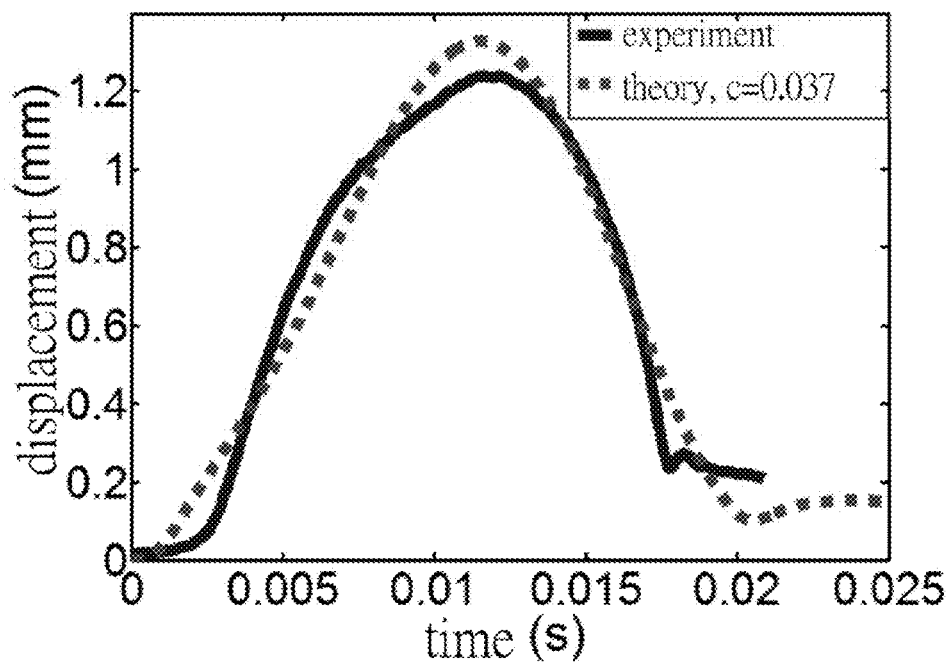
FIG. 8A is a schematic diagram of one patient's corneal displacement time series from the ophthalmotonometer and our model.
Figure 8B:
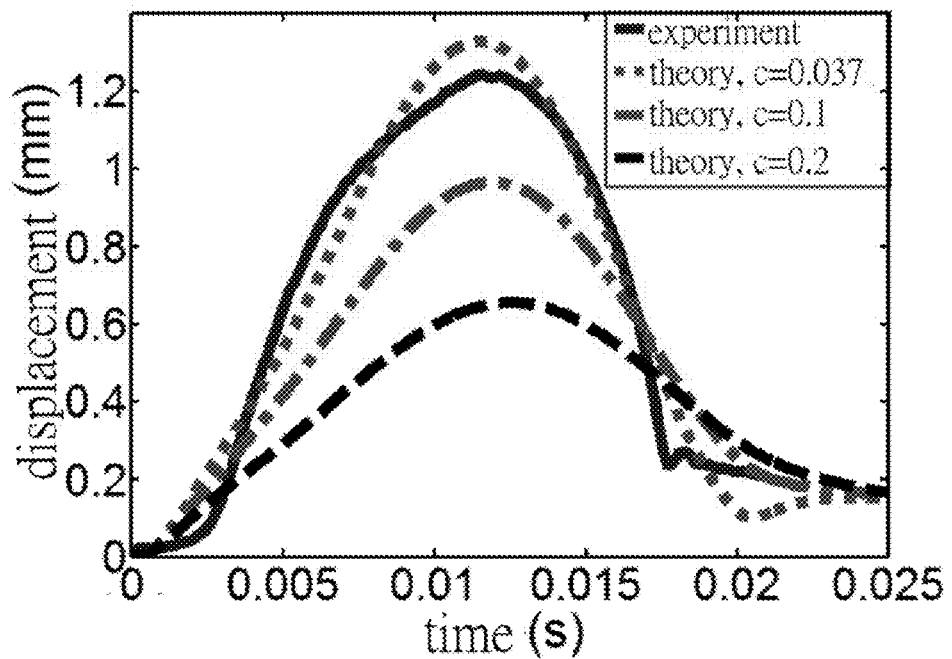
FIG. 8B is a schematic diagram of the damping ratio affections.

FIG. 8A shows one patient's corneal displacement time series measured from the ophthalmotonometer 12, and the same time series obtained from our model are also shown. The two curves are not perfectly close, because there are too many assumptions in the model. Besides, how to setup the boundary conditions is a big issue. From the calculation experience, the Young's modulus affects almost the first half oscillation of the duration; the damping ratio affects the dispersion in the last half of the duration as shown in FIG. 8B.

The above mentioned Table III shows the results of Young's moduli and the damping coefficients among the 25 patients. The average Young's modulus is about 0.3183 Mpa and the average damping coefficient is about 0.0456. These values satisfy the acceptable ranges 0.1~10 MPa from the tests of the human eyes (in vitro) as listed on Table IV.

TABLE IV

| No. | Researchers | Young's moduli [Mpa] | Remark | Years | References |
|---|---|---|---|---|---|
| 1 | Woo, SL-Y., et al | 1.8-8.1 | Human cadaver eyes, with I-3 days post mortem | 1972 | FIG. 6 in [19] |
| 2 | Jue, Bill, and David M. Maurice | 5 | Human cadaver eyes, aged between 45 and 90 year, obtained within 24 hour of death. | 1986 | [20] |
| 3 | Wang, Hsichun, et al. | 4.2-30 | Six human cadaver eye, aged 75-82 years, immersed in the 15% solution of saline, the other six ones in the dextran, aged 78-84 years. | 1996 | Table 1 in [21] |
| 4 | Uchio, Eiichi, et al. | 50-100 | Human cadaver eye enucleated between 8-24 hour and stored at 4° C., experiment conducting withing 48 hour | 1999 | FIG. 1(A) in [22] |
| 5 | Katherine D. Voorhies | 6.89-110.32 | Human cadaver eye Packaged in the saline gauze | 2003 | Table 8 in [23] |

TABLE IV-continued

| No. | Researchers | Young's moduli [Mpa] | Remark | Years | References |
|---|---|---|---|---|---|
| 6 | Elsheikh, Ahmed, Defu Wang, and David Pye | 0.16-0.81 | 36 human cadaver eye, immersed in the storage medium Optisol GS at 4° C. within 12 hours of death and tested within 14 days. | 2007 | [24] |
| 7 | Hamilton, Kirsten E., and David C. Pye | 0.13-0.43 | 100 living eyes, aged 18 between 30 years. The Orssengo-Pye algorithm is used. | 2008 | [25] |
| 8 | Elsheikh, Ahmed, Daad Alhasso, and Paolo Rama | 0.15-1.15 | Forty nine Human cadaver eyes preserved in the Eusol C, for a maximum of 12 hour of death, used in 5-7 day of preservation | 2008 | FIG. 6 in [26] |
| 9 | Cartwright, Nathaniel E. Knox, John R. Tyrer, and John Marshall | 0.27-0.52 | Human cadaver eyes, aged between 24 and 102 years, with 5-27 days post mortem, immersed in Eagle's minimal essential medium | 2011 | [27] |

Compared with the prior art, this application provides real-time dynamic model to estimate instantaneously the eyeball properties during the IOP measuring by the ophthalmotonometer.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A corneal examination method, comprising:
    (S1) reading an actual corneal deformation of a corneal of a tester from an ophthalmotonometer, wherein the ophthalmotonometer snaps corneal sectional images while blowing air onto the corneal, and generates the actual deformation according to the corneal sectional images;
    (S2) substituting a Young's modulus initial value and a damping coefficient initial value into a mathematical equation, wherein a calculated corneal deformation is obtained from a mathematical equation with the Young's modulus initial value and the damping coefficient initial value, and the mathematical equation is:

$$w(\theta, \phi; t) = \sum_{l=1}^{\infty} w_{l0}(\theta, \phi; t)$$

in which the term $w_{l0}$ is the measured displacement on corneal surface $$w_{l0}(\theta, \phi; t) = \frac{(2l+1)}{2M_l \omega_{Dl}} P_l(\cos\theta) \cdot \int_0^\pi g(\alpha) P_l(\alpha) \sin\alpha d\alpha \cdot \int_0^t e^{-\xi_l \omega_{Dl} t} \sin\omega_{Dl}(t-\tau) s(t) d\tau$$

where $M_l$ is modal mass $$M_l = \rho \cdot h + R\left(\frac{\rho^+}{l} + \frac{\rho^-}{l+1}\right),$$

modal frequency is $\omega_{Dl} = \omega_l \sqrt{1-\xi_l^2}$, $P_l(\cos\theta)$ is the Legendre polynomials, $g(\alpha)$ is the air pressure distribution on corneal surface, $\xi_l$ is modal damping ratio, $s(t)$ is the air puff time history, R is the corneal radius, h is the thickness of the diaphragm, $\rho$ is the cornea density, $\rho^+$ and $\rho^-$ are densities inside and outside the cornea, l is the modal order, $$\omega_l^2 = \frac{\frac{(E+T)\cdot h^3}{12(1-v^2)} \frac{l^3(l+1)^3}{R^4} + \frac{T \cdot h \cdot l^2(l+1)^2}{R^2}}{[(l+1)\rho^+ + l\cdot\rho^-]R + l(l+1)\rho \cdot h},$$

E is the Young's modulus, T is the tension on the diaphragm, and v is the Poisson's ratio, and images recorded from tonometer could provide the s(t), R, and h, and the densities, $\rho$, $\rho^+$ and $\rho^-$ are given from normal values, $\xi_l$ is given 3~5%, T is obtained from the intraocular pressure, v is assumed 0.4~0.49;
    (S3) determining whether error amount between the calculated deformation and the actual deformation is a minimum or not; and
    (S4) determining the Young's modulus initial value and the damping coefficient initial value as a Young's modulus and a damping coefficient of the corneal, and judging whether the tester's corneal have disease, wherein the disease includes induced flaucoma, retinal lesion.

2. The algorithm as claimed in claim 1, if the determining in the step (S3) is not, then back to the step (S2) and iterate in optimization until the error amount is a minimum.

3. The algorithm as claimed in claim 1, wherein the minimum is $10^{-3}$.

4. A corneal dynamic model system, comprising:
an ophthalmotonometer, directing an external force to eyeball, and snapping corneal sectional images, generating an actual corneal deformation Dt;
a calculating unit, connected to the ophthalmotonometer, wherein the calculating units acquires the actual corneal deformation from the ophthalmotonometer, and substituting a Young's modulus initial value and a damping coefficient initial value into a mathematical equation, wherein a calculated corneal deformation is obtained from a mathematical equation with the Young's modulus initial value and the damping coefficient initial value, and the mathematical equation is:

$$w(\theta, \phi; t) = \sum_{l=1}^{\infty} w_{l0}(\theta, \phi; t)$$

in which the term $w_{l0}$ is the measured displacement on corneal surface $$w_{l0}(\theta, \phi; t) = \frac{(2l+1)}{2M_l \omega_{Dl}} P_l(\cos\theta) \cdot \int_0^{\pi} g(\alpha) P_l(\alpha) \sin\alpha d\alpha \cdot \int_0^t e^{-\xi_l \omega_{Dl} t} \sin\omega_{Dl}(t-\tau) s(t) d\tau$$

where $M_l$ is modal mass $$M_l = \rho \cdot h + R\left(\frac{\rho^+}{l} + \frac{\rho^-}{l+1}\right),$$

modal frequency is $\omega_{Dl} = \omega_l \sqrt{1-\xi_l^2}$, $P_l(\cos\theta)$ is the Legendre polynomials, $g(\alpha)$ is the air pressure distribution on corneal surface, $\xi_l$ is modal damping ratio, s(t) is the air puff time history, R is the corneal radius, h is the thickness of the diaphragm, $\rho$ is the cornea density, $\rho^+$ and $\rho^-$ are densities inside and outside the cornea, l is the modal order, $$\omega_l^2 = \frac{\frac{(E+T)\cdot h^3}{12(1-v^2)} \frac{l^3(l+1)^3}{R^4} + \frac{T \cdot h \cdot l^2(l+1)^2}{R^2}}{[(l+1)\rho^+ + l\cdot\rho^-]R + l(l+1)\rho \cdot h},$$

E is the Young's modulus, T is the tension on the diaphragm, and v is the Poisson's ratio, and images recorded from tonometer could provide the s(t), R, and h, and the densities, $\rho$, $\rho^+$ and $\rho^-$ are given from normal values, $\xi_l$ is given 3~5%, T is obtained from the intraocular pressure, v is assumed 0.45~0.49, and the calculation unit determines whether error amount between the calculated deformation and the actual deformation is a minimum or not; and determines the Young's modulus initial value and the damping coefficient initial value as a Young's modulus and a damping coefficient of the corneal, and judging whether the tester's corneal have disease, wherein the disease includes induced glaucoma, retinal lesion.

5. The system as claimed in claim 4, if the determining in the step (S3) is not, then back to the step (S2) and iterate in optimization until the error amount is a minimum.

6. The system as claimed in claim 4, wherein the minimum is $10^{-3}$.

* * * * *